United States Patent
Wu et al.

(10) Patent No.: US 11,617,891 B2
(45) Date of Patent: Apr. 4, 2023

(54) IMPLANTABLE MEDICAL DEVICE HAVING PACKAGE AND METHOD FOR PACKAGING IMPLANTABLE MEDICAL DEVICE

(71) Applicant: Shenzhen CAS-Envision Medical Technology Co., Ltd, Shenzhen (CN)

(72) Inventors: Tianzhun Wu, Shenzhen (CN); Saisai Zhao, Shenzhen (CN); Ye Feng, Shenzhen (CN); Chunlei Yang, Shenzhen (CN)

(73) Assignee: Shenzhen CAS-Envision Medical Technology Co., Ltd, Guangdong (CN)

( * ) Notice: Subject to any disclaimer, the term of this patent is extended or adjusted under 35 U.S.C. 154(b) by 373 days.

(21) Appl. No.: 16/622,538

(22) PCT Filed: Jul. 21, 2017

(86) PCT No.: PCT/CN2017/093873
§ 371 (c)(1),
(2) Date: Dec. 13, 2019

(87) PCT Pub. No.: WO2019/014926
PCT Pub. Date: Jan. 24, 2019

(65) Prior Publication Data
US 2020/0101304 A1 Apr. 2, 2020

(51) Int. Cl.
*A61N 1/375* (2006.01)
*A61N 1/36* (2006.01)
(Continued)

(52) U.S. Cl.
CPC ........ *A61N 1/37512* (2017.08); *A61F 2/0095* (2013.01); *A61F 2/14* (2013.01);
(Continued)

(58) Field of Classification Search
CPC .. A61N 1/37512; A61N 1/05; A61N 1/36038; A61N 1/375; A61N 1/3758;
(Continued)

(56) References Cited

U.S. PATENT DOCUMENTS

| 2003/0120320 A1* | 6/2003 | Solom | H01G 9/008 607/36 |
|---|---|---|---|
| 2004/0134821 A1 | 7/2004 | Tornier | |

(Continued)

FOREIGN PATENT DOCUMENTS

| CN | 1160533 A | 10/1997 |
|---|---|---|
| CN | 103118649 A | 5/2013 |

(Continued)

OTHER PUBLICATIONS

International Search Report dated Apr. 26, 2018 in corresponding International Application No. PCT/CN2017/093873; 7 pages.

*Primary Examiner* — Eugene T Wu
(74) *Attorney, Agent, or Firm* — Maier & Maier, PLLC

(57) ABSTRACT

An implantable medical device having a package, including: a device body, and a package configured for packaging the device body. The package includes at least one organic film layer and at least one inorganic film layer that are stacked on one another. An innermost layer of the package is an organic film layer or an inorganic film layer, and an outermost layer of the package is an organic film layer or an inorganic film layer. Each organic film layer is a parylene film or polyimide resin film with biocompatibility, and each inorganic film layer is an inorganic film with biocompatibility. A method for packaging an implantable medical device is also provided.

5 Claims, 3 Drawing Sheets

(51) Int. Cl.
  *A61F 2/14* (2006.01)
  *B05D 1/00* (2006.01)
  *C23C 16/40* (2006.01)
  *C23C 16/455* (2006.01)
  *A61J 1/00* (2023.01)
  *A61F 2/00* (2006.01)
  *A61N 1/05* (2006.01)

(52) U.S. Cl.
  CPC .............. *A61J 1/00* (2013.01); *A61N 1/05* (2013.01); *A61N 1/36038* (2017.08); *A61N 1/375* (2013.01); *A61N 1/3758* (2013.01); *B05D 1/60* (2013.01); *C23C 16/403* (2013.01); *C23C 16/45525* (2013.01)

(58) Field of Classification Search
  CPC .. A61F 2/0095; A61F 2/14; A61J 1/00; B05D 1/60; B05D 7/56; B05D 1/02; B05D 3/0254; B05D 5/083; B05D 7/52; C23C 16/403; C23C 16/45525; C23C 16/45555
  See application file for complete search history.

(56) References Cited

U.S. PATENT DOCUMENTS

| | | | |
|---|---|---|---|
| 2011/0039050 A1* | 2/2011 | Hogg | H05K 3/284 |
| | | | 427/2.24 |
| 2016/0133540 A1* | 5/2016 | Tai | H01L 23/3135 |
| | | | 257/790 |
| 2018/0331328 A1* | 11/2018 | Won | H01L 51/5253 |

FOREIGN PATENT DOCUMENTS

| | | |
|---|---|---|
| CN | 104070744 A | 10/2014 |
| CN | 104736194 A | 6/2015 |
| CN | 105517946 A | 4/2016 |

\* cited by examiner

IMPLANTABLE MEDICAL DEVICE HAVING PACKAGE AND METHOD FOR PACKAGING IMPLANTABLE MEDICAL DEVICE

CROSS-REFERENCE TO RELATED APPLICATIONS

This application is a U.S. National Stage of International Patent Application No. PCT/CN2017/093873 filed on Jul. 21, 2017. The aforementioned application is hereby incorporated by reference in its entirety

FIELD

The present application relates to the technical field of package of implantable medical devices, and more particularly to an implantable medical device having a package and a method for packaging an implantable medical device.

BACKGROUND

With the development of medical technology, medical devices trend to be miniaturized and intelligent. Implantable medical devices with functions of information sensing and processing, including cardiac pacemakers, cochlear implants, and deep brain stimulators, are available on the market and provide completely new solutions to a variety of diseases that are difficult to be treated by conventional medicines. However, such implantable medical devices are particularly sensitive to water vapor and oxygen in body fluid, thus requiring excellent packages to ensure their performances and service lives.

At present, the relatively mature hard packaging (using plastic, metal, ceramic, or silicon substrate for direct packaging) on the market cannot ensure that the electronic device will sustain in a water-free environment for a long period, and a closed cavity with mechanical support performance and biocompatible performance is required. As a result, the cost of the implantable package is extremely high, accounting for more than 30% of that of the implantable medical device. In addition, with the rapid development of society and human requirements for future technologies, demands for the number of the substrate channels of the implantable package will become greater and denser. However, it is difficult for the high-density electronic devices to realize small volume implantation by using the conventional hard packaging process and method, and the function realization of the implantable device is greatly restricted.

Polymer packaging and thin film packaging are main flexible packaging methods and are widely used in the field of liquid crystal display (LED) packaging due to light weight, high strength, high temperature resistance, and small size. In order to effectively reduce the cost of the implantable medical device, satisfy the requirements of small-volume and high-density packaging, and improve the implantation life, a feasible flexible packaging solution for the implantable medical device is desired.

SUMMARY

In view of the above, it is an object of the present application to provide an implantable medical device having a package and a method for packaging an implantable medical device. By stacking the organic and inorganic films to form the package with excellent biocompatibility, water and oxygen permeation paths in the complex environment inside the body extend along interfaces of the organic/inorganic films, thus, the water and oxygen permeation paths are greatly extended, the water and oxygen environment can be well isolated, which greatly improves the service life of the implantable device, and effectively tackles the problem in the implantation life of the conventional package for the implantable medical device.

Specifically, in one aspect, the present application provides an implantable medical device having a package, which comprises: a device body, and a package configured for packaging the device body. The package comprises at least one organic film layer and at least one inorganic film layer that are stacked on one another. An innermost layer of the package is an organic film layer or an inorganic film layer, and an outermost layer of the package is an organic film layer or an inorganic film layer. Each organic film layer is a parylene film or polyimide resin film with biocompatibility, and each inorganic film layer is an inorganic film with biocompatibility.

The implantable medical device of the present application adopts the organic film and inorganic film with biocompatibility as the package materials to form the package. The package not only has excellent biocompatibility to enable the implantation life of the device to satisfy the requirement, but also can well isolate the device from the water and oxygen environment in the body fluid of human body thereby ensuring the normal operation of the device. In addition, this kind of film package can greatly reduce the volume of the implant and be applicable to the package of high-density electronic devices (such as 1000-channel chip sensor), which highly satisfies the requirements of the function and performance of the implanted product and addresses the requirement of product flexibility.

The inorganic film with biocompatibility comprises an $Al_2O_3$ film, a $SiO_2$ film, a SiC film, a $TiO_2$ film, or a SiN film The inorganic film has not only good biocompatibility but also excellent water and oxygen isolation performance. By stacking the inorganic films and the organic films on one another to form a multi-layered dense structure, the water and oxygen permeation paths can be greatly extended, and therefore the device body can be effectively protected.

Each organic film layer has a thickness of 0.5-60 μm, and further, the thickness of each organic film layer may be 1-25 μm, 5-20 μm, or 30-55 μm. Each inorganic film layer has a thickness of 20-100 nm, and further, the thickness of the inorganic film layer may be 30-90 nm, 50-70 nm, or 60-80 nm. A suitable thickness can not only ensure the excellent binding of respective layers, but also obtain better performance of water and oxygen isolation.

The parylene film with biocompatibility as the organic film layer may be parylenes with structures of an N type, a C type, a D type, or an HT type.

In the present application, the organic film layers and the inorganic film layers are alternately stacked.

In the present application, the numbers of the organic film layers and the inorganic film layers can be designed according to the requirement on the implantation life of the implantable device. For those required to have a longer implantation life, the numbers of the organic film layers and the inorganic film layers increase correspondingly, generally, a total number of the organic film layers and the inorganic film layers is equal to or greater than 2. Specifically, for example, the number of the organic film layers and the number of the inorganic film layers are designed to between 2 and 10, respectively. In the case that the number of the organic film layers and the number of the inorganic film layers are greater than 1, respectively, the layers may be respectively numbered as a first organic film layer, a second organic film layer, . . . , and a first inorganic film layer, a second inorganic film layer, . . . . Materials for the organic film layers may be the same or different. Materials for the inorganic film layers may be the same or different.

In order to further improve the package effect of the package, the package further comprises one or more organic buffer layers, and each organic buffer layer is a polytetrafluoroethylene film or polytetrafluoroethylene-like fluorocarbon polymer film with biocompatibility. The polytetrafluoroethylene film and the polytetrafluoroethylene-like fluorocarbon polymer film are purely inert materials, which have strong biological adaptation, thereby not causing body rejection or physiological side effects on human body, and have microporous structures, which can play a good buffering function in the package and at the same time further enhancing the binding force between the organic film layer and the inorganic film layer.

Each organic buffer layer is arranged above any of the organic film layer and the inorganic film layer, that is, the organic buffer layer is sandwiched between any two adjacent organic film layers, or sandwiched between any two adjacent inorganic film layers, or sandwiched between any two adjacent organic film layer and inorganic film layer, or arranged as an uttermost layer of the package.

Each organic buffer layer has a thickness of 0.5-60 μm. Further, the thickness of the organic buffer layer may be 1-25 μm, 5-20 μm, or 30-55 μm. The number of the organic buffer layers can be designed according to the requirement on the implantation life of the implantable device. For those required to have a longer implantation life, the number of the organic buffer layer increases correspondingly, specifically, for example, the number of the organic buffer layers may be 1-10. In the case that the number of the organic buffer layers is greater than 1, the organic buffer layers can be numbered as a first organic buffer layer, a second organic buffer layer . . . . Materials for the organic buffer layers may be the same or different.

In the present application, the device body comprises one or more selected from a neural electrode, a wireless transmission coil, an integrated circuit chip, a printed circuit board, a sensor, a biochip board, a cardiac pacemaker, an artificial retina, a cochlear implant, a defibrillator, and a stimulator. The stimulator includes: a vagus nerve stimulator, a spinal cord stimulator, a carotid sinus electrical stimulator, a bladder stimulator, a gastrointestinal stimulator, and a deep brain stimulator. The package of the present application may be arranged outside an integral device, or outside a certain part of the integral device, which can be designed according to practical needs.

In the implantable medical device with the package provided according to the first aspect of the present application, the package has excellent biocompatibility and can isolate water vapor and oxygen at the same time, thereby protecting the normal operation of the implantable device, prolonging the service life of the device and satisfying the requirement of multi-year implantation life. In addition, this package can also satisfy the package requirement of implantable high-density electronic device.

In a second aspect, the present application provides a method for packaging an implantable medical device. The method comprises:

providing a device body, and preparing at least one organic film layer and at least one inorganic film layer on a surface of the device body to form a package. Each organic film layer is a parylene film or polyimide resin film with biocompatibility, and each inorganic film layer is an inorganic film with biocompatibility. An innermost layer of the package is an organic film layer or an inorganic film layer, and an outermost layer of the package is an organic film layer or an inorganic film layer.

In the packaging method of the present application, the device body comprises one or more selected from a neural electrode, a wireless transmission coil, an integrated circuit chip, a printed circuit board, a sensor, a biochip board, a cardiac pacemaker, an artificial retina, a cochlear implant, a defibrillator, and a stimulator. The stimulator includes: a vagus nerve stimulator, a spinal cord stimulator, a carotid sinus electrical stimulator, a bladder stimulator, a gastrointestinal stimulator, and a deep brain stimulator.

The parylene film with biocompatibility as the organic film layer may be parylenes with structures of an N type, a C type, a D type, or an HT type. Each organic film layer has a thickness of 0.5-60 μm, and further, the thickness of each organic film layer may be 1-25 μm, 5-20 μm, or 30-55 μm. The organic film layer can be prepared by chemical vapor deposition (CVD), spin coating, or dip-coating, and the prepared film can provide a very smooth, continuous, and defect-free film on any shape or curved surface, which also makes the package of the heterogeneous composite film possible, thereby significantly reducing the package size.

The inorganic film with biocompatibility comprises: an $Al_2O_3$ film, a $SiO_2$ film, a SiC film, a $TiO_2$ film, or a SiN film. Each inorganic film layer has a thickness of 20-100 nm, and further, the thickness of the inorganic film layer may be 30-90 nm, 50-70 nm, or 60-80 nm. The inorganic film layer can be prepared by chemical vapor deposition (CVD), spin coating, or dip-coating, and the prepared film can provide a very smooth, continuous, and defect-free film on any shape or curved surface, which also makes the package of the heterogeneous composite film possible, thereby significantly reducing the package size.

In the packaging method of the present application, the numbers of the organic film layers and the inorganic film layers can be designed according to the requirement on the implantation life of the implantable device. For those required to have a longer implantation life, the numbers of the organic film layers and the inorganic film layers and the thicknesses thereof increase correspondingly, generally, a total number of the organic film layers and the inorganic film layers is equal to or greater than 2. Specifically, for example, the number of the organic film layers and the number of the inorganic film layers are designed to between 2 and 10, respectively.

In the present application, the method further comprises: preparing an organic buffer layer on a surface of any of the organic film layer and the inorganic film layer, and the organic buffer layer is a polytetrafluoroethylene film or polytetrafluoroethylene-like fluorocarbon polymer film with biocompatibility. Each organic buffer layer may be sandwiched between any two adjacent organic film layers, or sandwiched between any two adjacent inorganic film layers, or sandwiched between any two adjacent organic film layer and inorganic film layer, or arranged as an uttermost layer of the package. The organic buffer layer may be prepared by dip-coating or spraying.

Each organic buffer layer has a thickness of 0.5-60 μm. Further, the thickness of the organic buffer layer may be 1-25 μm, 5-20 μm, or 30-55 μm. The number of the organic buffer layers can be designed according to the requirement on the implantation life of the implantable device. For those required to have a longer implantation life, the number of the organic buffer layer increases correspondingly, specifically, for example, the number of the organic buffer layers may be 1-10.

In the packaging method of the present application, each time before preparation of the inorganic film layer, the organic film layer or the organic buffer layer is annealed at a temperature of 100-200° C. for 5-120 minutes. After annealing, a binding force between the inorganic film layer and the surface of the organic film layer or the organic buffer layer can be effectively enhanced to avoid the delamination problem between the interfaces, thereby obtaining a dense organic-inorganic film layer.

The method for packaging the implantable medical device provided by the second aspect of the present application is applied to the field of active implantable medical devices, and can effectively solve the packaging problem of the existing active implant. The present packaging method can not only greatly reduce the cost but also satisfy the requirements on the package of the implantable high-density electronic device.

Advantages of the present application will be partially described hereinbelow in the specification, other parts of the advantages of the present application may be obvious according to the specification or may be obtained from the implementation of embodiments of the present application.

DETAILED DESCRIPTION OF THE EMBODIMENTS

Preferred embodiments of the present application are described hereinbelow. It should be understood that for those skilled in the art, some improvements and modifications may be made without departing from the principles of the embodiments of the present application, and such improvements and modifications may be considered to be within the protection scope of the embodiments of the present application.

Embodiment 1

Figure 1:
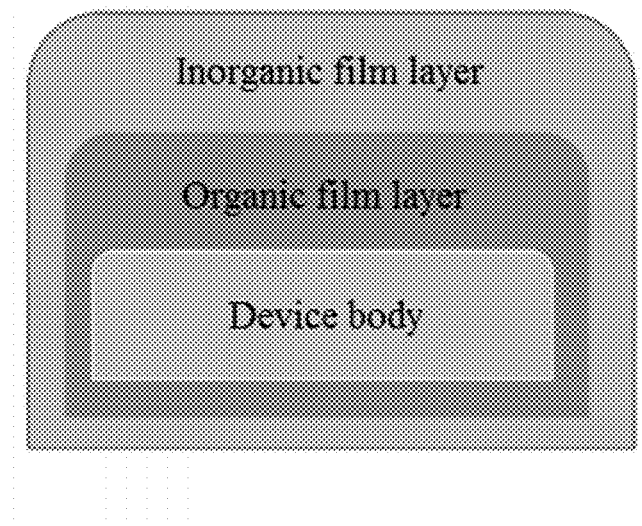
FIG. 1 is a structural diagram of an implantable medical device having a package prepared by Embodiment 1 of the present application.

A method for packaging an implantable medical device, included the following steps:

1) an implantable device body was provided, an organic film layer having a thickness of 60 μm was prepared on a surface of the device body by chemical vapor deposition, in which, the organic film layer was a parylene film; thereafter, an annealing treatment was performed at 150° C. for 2 hrs; and 2) an inorganic film layer having a thickness of 100 nm was prepared on the organic film layer by atomic layer deposition, thus obtaining a package. The inorganic film layer was an $Al_2O_3$ film The implantable medical device having a package obtained by the present embodiment was shown in FIG. 1. The package was in a double-layered structure, which included the organic film layer and the inorganic film layer sequentially arranged on the surface of the implantable device body.

Embodiment 2

Figure 2:
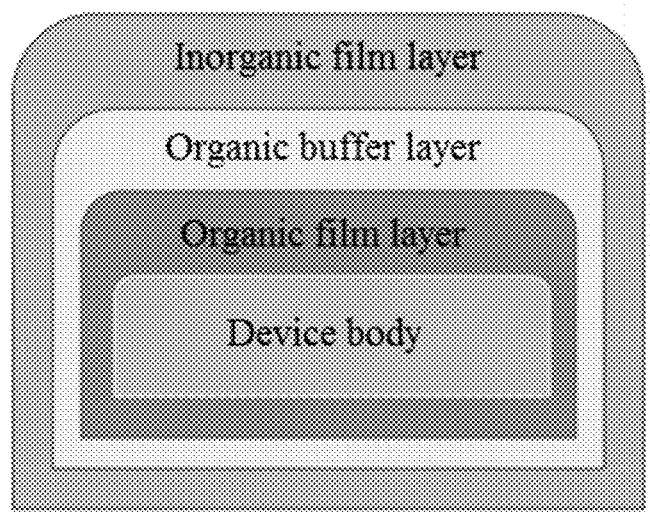
FIG. 2 is a structural diagram of an implantable medical device having a package prepared by Embodiment 2 of the present application.

A method for packaging an implantable medical device, included the following steps:

1) an implantable device body was provided, an organic film layer having a thickness of 20 μm was prepared on a surface of the device body by spin coating, of which, the organic film layer was a polyimide resin film;

2) an organic buffer layer having a thickness of 30 μm was prepared on a surface of the organic film layer by spray coating and annealed at 150° C. for 1 hr; the organic buffer layer was a polytetrafluoroethylene-like fluorocarbon polymer film; and 3) after the annealing, an inorganic film layer having a thickness of 80 nm was prepared on the organic buffer layer by atomic layer deposition, thus obtaining a package. The inorganic film layer was an $Al_2O_3$ film. The implantable medical device having a package prepared by the present embodiment was shown in FIG. 2. The package was in a three-layered structure which included: the organic film layer, the organic buffer layer, and the inorganic film layer sequentially arranged on the surface of the device body.

Embodiment 3

Figure 3:
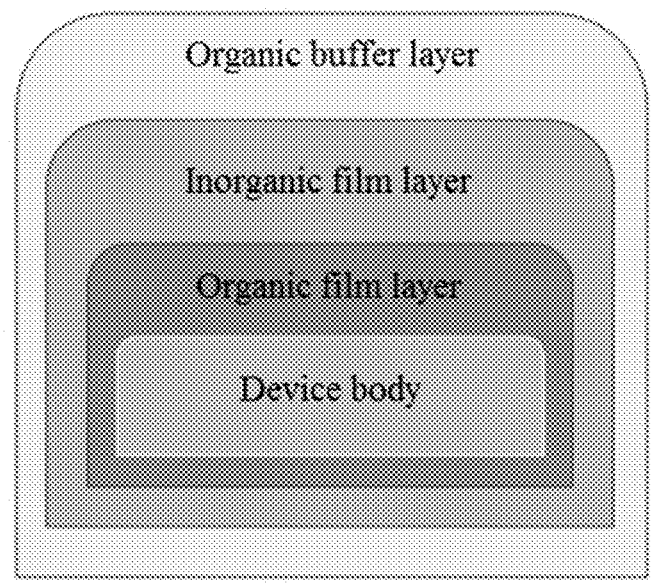
FIG. 3 is a structural diagram of an implantable medical device having a package prepared by Embodiment 3 of the present application.

A method for packaging an implantable medical device, included the following steps:

1) an implantable device body was provided, an organic film layer having a thickness of 30 μm was prepared on a surface of the device body by chemical vapor deposition, and annealed at 180° C. for 30 mins; the organic film layer was a parylene film;

2) after annealing, an inorganic film layer having a thickness of 70 nm was prepared on the organic film layer by atomic layer deposition, thus obtaining the package. The inorganic film layer was a $SiO_2$ film; and 3) an organic buffer layer having a thickness of 25 μm was prepared on a surface of the inorganic film layer by spray coating. The organic buffer layer was a polytetrafluoroethylene-like fluorocarbon polymer film. The implantable medical device having a package prepared by the present embodiment was shown in FIG. 3, the package was a three-layered structure which included: the organic film layer, the inorganic film layer, and the organic buffer layer sequentially arranged on the surface of the device body.

Embodiment 4

Figure 4:
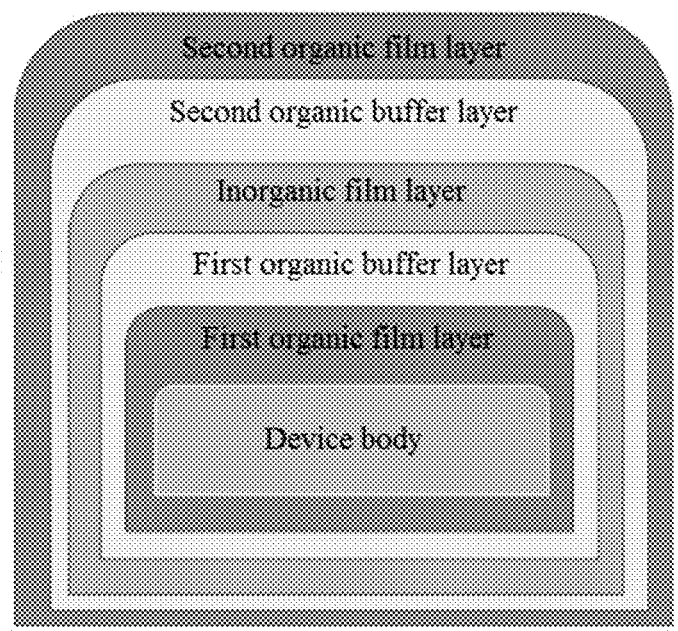
FIG. 4 is a structural diagram of an implantable medical device having a package prepared by Embodiment 4 of the present application.

A method for packaging an implantable medical device, included the following steps:

1) an implantable device body was provided, a first organic film layer having a thickness of 10 μm was prepared on a surface of the device body by dip-coating, and the first organic film layer was a polyimide resin film;

2) a first organic buffer layer having a thickness of 20 μm was prepared on a surface of the first organic film layer by spray coating and annealed at 150° C. for 1.5 hrs; the first organic buffer layer was a polytetrafluoroethylene-like fluorocarbon polymer film;

3) after annealing, an inorganic film layer having a thickness of 80 nm was prepared on the first organic buffer layer by atomic layer deposition, in which, the inorganic film layer was a SiC film;

4) a second organic buffer layer having a thickness of 10 μm was prepared on a surface of the inorganic film layer by spray coating, in which, the second organic buffer layer was a polytetrafluoroethylene-like fluorocarbon polymer film; and 5) a second organic film layer with a thickness of 15 μm was prepared on the second organic buffer layer by chemical vapor deposition, thus obtaining a package. The second organic film layer was a parylene film. The implantable medical device having a package prepared by the present embodiment was shown in FIG. 4. The package has a five-layered structure, which included: the first organic film layer, the first organic buffer layer, the inorganic film layer, the second organic buffer layer, and the second organic film layer sequentially arranged on the surface of the implantable device body.

Embodiment 5

A method for packaging an implantable medical device, included the following steps:

1) an implantable device body was provided, a first organic film layer having a thickness of 20 μm was prepared on a surface of the device body by chemical vapor deposition, and annealed at 150° C. for 40 mins, in which, the first organic film layer was a parylene film;

2) after annealing, a first inorganic film layer having a thickness of 40 nm was prepared on the first organic buffer layer by atomic layer deposition, where the inorganic film layer was an $Al_2O_3$ film;

3) an organic buffer layer having a thickness of 10 μm was prepared on a surface of the inorganic film layer by spray coating, the organic buffer layer was a polytetrafluoroethylene-like fluorocarbon polymer film.

Figure 5:
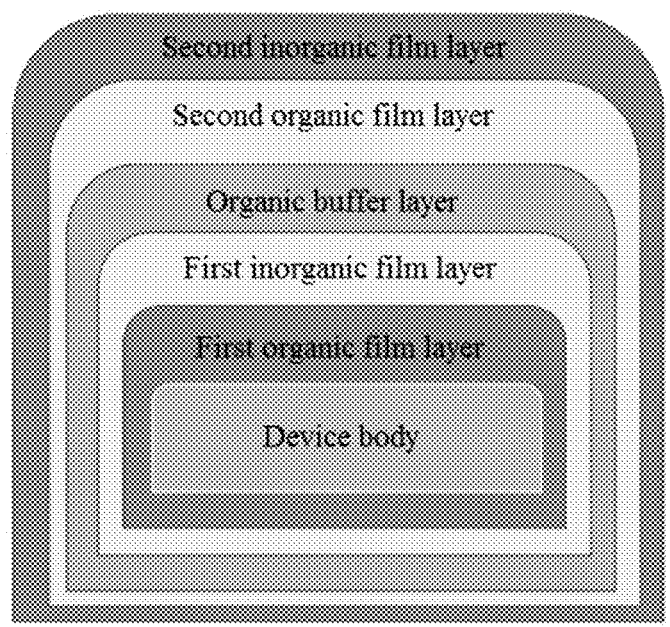
FIG. 5 is a structural diagram of an implantable medical device having a package prepared by Embodiment 5 of the present application.

4) a second organic film layer having a thickness of 15 μm was prepared on the organic buffer layer by chemical vapor deposition, and annealed at 150° C. for 40 mins, in which, the second organic film layer was a polyimide resin film; and 5) after annealing, a second inorganic film layer having a thickness of 30 nm was prepared on the second organic film layer by atomic layer deposition, thus obtaining a package, and the second inorganic film layer was an $Al_2O_3$ film The implantable medical device having a package prepared by the present embodiment was shown in FIG. 5. The package had a five-layered structure, which included: the first organic film layer, the first inorganic film layer, the organic buffer layer, the second organic film layer, and the second inorganic film layer sequentially arranged on the surface of the implantable device body.

Embodiment 6

Figure 6:
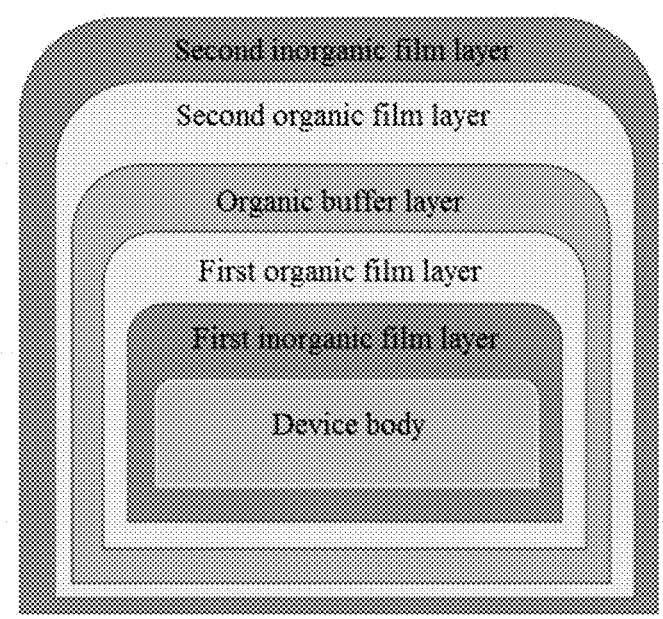
FIG. 6 is a structural diagram of an implantable medical device having a package prepared by Embodiment 6 of the present application.

A method for packaging an implantable medical device, included the following steps:

1) an implantable device body was provided, a first inorganic film layer having a thickness of 40 μm was prepared on a surface of the device body by atomic layer deposition, and the first organic film layer was an $Al_2O_3$ film;

2) a first organic film layer having a thickness of 20 μm was prepared on the first inorganic film layer by chemical vapor deposition; the first organic film layer was a parylene film;

3) an organic buffer layer having a thickness of 10 μm was prepared on the first organic film layer by spray coating; the organic buffer layer was a polytetrafluoroethylene-like fluorocarbon polymer film;

4) a second organic film layer having a thickness of 15 μm was prepared on the organic buffer layer by chemical vapor deposition, and annealed at 150° C. for 40 mins, in which, the second organic film layer was a polyimide resin film; and 5) after annealing, a second inorganic film layer having a thickness of 30 nm was prepared on the second organic film layer by atomic layer deposition, thus obtaining a package. The second inorganic film layer was an $Al_2O_3$ film The implantable medical device having a package prepared by the present embodiment was shown in FIG. 6. The package had a five-layered structure, which included: the first inorganic film layer, the first organic film layer, the organic buffer layer, the second organic film layer, and the second inorganic film layer sequentially arranged on the surface of the implantable device body.

Only some of embodiments are described in the above embodiments of the present application, in other embodiments, the structure of the package may be modified with the protection scope of the claims of the present application.

In the above embodiments of the present application, the device body comprises one or more selected from a neural electrode, a wireless transmission coil, an integrated circuit chip, a printed circuit board, a sensor, a biochip board, a cardiac pacemaker, an artificial retina, a cochlear implant, a defibrillator, and a stimulator. The stimulator includes: a vagus nerve stimulator, a spinal cord stimulator, a carotid sinus electrical stimulator, a bladder stimulator, a gastrointestinal stimulator, and a deep brain stimulator.

In the implantable medical devices having a package prepared by the above embodiments of the present application, the package is formed by stacking a plurality of organic and inorganic dense films with biocompatibility, thereby having a uniform thickness and being dense, pinhole-free, transparent, and stress-free, and having excellent water and oxygen insulation and proof. After implanting the implanted device into the human body, the permeation paths of water and oxygen molecules in the complex environment of the body will extend along the interfaces of the organic/the inorganic films, thus, the water and oxygen permeation paths are greatly extended, the water and oxygen environment can be well isolated, which greatly improves the service life of the implantable device.

Effect Embodiment

In order to strongly support the beneficial effects brought by the technical solutions of the embodiments of the present application, the following performance tests were performed:

The implantable medical devices having a package prepared by the above embodiments of the present application were performed with a relative growth rate toxicity test and a helium leak test. The relative growth rate toxicity test can effectively reflect the biocompatibility of the implantable device, while the helium leak test can well reflect the reliability of implantation life of the device.

Cytotoxicity test refers to the national standard GB/T 16886.5-2003 of the People's Republic of China. Table 1 shows results of the relative growth rate toxicity test of the implantable medical device having a package prepared in Embodiments 1-6 of the present application.

TABLE 1

| Groups | Absorbance value of Embodiment 1 | Absorbance value of Embodiment 2 | Absorbance value of Embodiment 3 | Absorbance value of Embodiment 4 | Absorbance value of Embodiment 5 | Absorbance value of Embodiment 6 |
|---|---|---|---|---|---|---|
| 1 | 0.247 | 0.252 | 0.256 | 0.265 | 0.251 | 0.254 |
| 2 | 0.284 | 0.267 | 0.223 | 0.233 | 0.229 | 0.265 |
| 3 | 0.254 | 0.262 | 0.298 | 0.283 | 0.273 | 0.275 |
| 4 | 0.282 | 0.275 | 0.244 | 0.259 | 0.247 | 0.248 |
| 5 | 0262 | 0.257 | 0.264 | 0.268 | 0.256 | 0.273 |
| 6 | 0.246 | 0.259 | 0.266 | 0.265 | 0.254 | 0.258 |
| Average absorbance value | 0.261833 | 0.262 | 0.257833 | 0.251667 | 0.253785 | 0.257455 |
| Relative growth rate | 1.033554 | 1.034212 | 1.023827 | 1.028757 | 1.027335 | 1.032454 |
| Grading | 0 | 0 | 0 | 0 | 0 | 0 |

It can be seen from the results of Table 1 that the cytotoxicity test of the implantable medical devices having a package prepared in Embodiments 1-6 of the present application had a cell grading of 0, good biocompatibility, and were able to be implanted inside the body for a long period.

The helium leak test showed that the implantable medical devices having the package prepared in Embodiments 1-6 of the present application were able to satisfy a 10-year implantation life standard.

It should be noted that those skilled in the art to which the present application pertains may also make modifications and changes to the embodiments described in the above. Thus, the present application is not limited to the specific embodiments disclosed and described in the above, and equivalents of the present application are intended to be included within the protection scope of the appended claims. In addition, although specific terms are used in the specification, these terms are merely for convenience of description and do not limit the application.

What is claimed is:

1. An implantable medical device having a package, comprising:
   a device body, and
   a package configured for packaging the device body, the package comprising a plurality of film layers, the plurality of film layers comprising at least one organic film layer and at least one inorganic film layer that are stacked on one another; wherein
   an innermost layer of the package is an organic film layer or an inorganic film layer, and an outermost layer of the package is an organic film layer or an inorganic film layer; and
   each organic film layer is a polyimide resin film with biocompatibility, and each inorganic film layer is an inorganic film with biocompatibility;
   the package further comprises one or more organic buffer layers, and each organic buffer layer is a polytetrafluoroethylene-like fluorocarbon polymer film with biocompatibility; and
   each organic buffer layer is sandwiched between two adjacent film layers, and at least one of the two adjacent film layers is the organic film layer.

2. The implantable medical device having a package according to claim 1, wherein the inorganic film with biocompatibility comprises: an $Al_2O_3$ film, a $SiO_2$ film, a SiC film, a $TiO_2$ film, or a SiN film.

3. The implantable medical device having a package according to claim 1, wherein the organic film layer has a thickness of 0.5-60 μm, and the inorganic film layer has a thickness of 20-100 nm.

4. The implantable medical device having a package according to claim 1, wherein each organic buffer layer has a thickness of 0.5-60 μm.

5. The implantable medical device having a package according to claim 1, wherein the device body comprises one or more selected from a neural electrode, a wireless transmission coil, an integrated circuit chip, a printed circuit board, a sensor, a biochip board, a cardiac pacemaker, an artificial retina, a cochlear implant, a defibrillator, and a stimulator.

* * * * *